United States Patent [19]
Weston

[11] Patent Number: 5,405,352
[45] Date of Patent: Apr. 11, 1995

[54] SUTURE KNOT, METHOD FOR ITS FORMATION AND USE, AND KNOT FORMING APPARATUS

[76] Inventor: Peter V. Weston, 705 Oak Hills Med. Bldg., 7711 Louis Pasteur Dr., San Antonio, Tex. 78229

[21] Appl. No.: 682,345
[22] Filed: Apr. 9, 1991
[51] Int. Cl.6 ............................................. A61B 17/00
[52] U.S. Cl. .................................. 606/148; 606/139; 284/1.2; 284/17
[58] Field of Search ............... 606/228, 148, 144, 139; 289/1, 17; 16/202, 207

[56] References Cited
U.S. PATENT DOCUMENTS

| | | | |
|---|---|---|---|
| 2,012,776 | 8/1935 | Roeder | 606/139 |
| 3,985,138 | 10/1976 | Jarvik | 606/144 |
| 4,935,027 | 6/1990 | Yoon | 606/146 |
| 5,084,058 | 1/1992 | Li | 606/139 X |
| 5,129,912 | 7/1992 | Noda et al. | 606/148 |

Primary Examiner—Stephen C. Pellegrino
Assistant Examiner—Jeffrey A. Schmidt
Attorney, Agent, or Firm—David G. Henry

[57] ABSTRACT

Disclosed is a novel slipknot for use as a suture knot in surgical procedures along with a simplified method for such knot's formation and a pre-formed suture system which provides a protoknot of the novel suture knot mounted on a tubular member or a knot tightener having a channel passing therethrough. The protoknot is formed into a completed suture knot by straight-line passage of the standing part of the filament, to which the surgical needle is initially attached, through the tubular member or the channel of the knot tightener and disengagement of same from the filament after passage of the filament through the patient's tissue.

4 Claims, 13 Drawing Sheets

SUTURE KNOT, METHOD FOR ITS FORMATION AND USE, AND KNOT FORMING APPARATUS

BACKGROUND OF THE INVENTION

1. Field of The Invention

Applicant's invention relates suture knots, methods and apparatuses employed in forming suture knots, and methods of use of such knots and apparatuses.

2. Background Information

Most (but not all) knots preferably exhibit the characteristic of not slipping or becoming untied during their normally anticipated use(s). The principle feature of a knot which is least likely to slip or unintentionally become untied is that of having more rather than fewer distortions of the filament which forms the knot within the bounds of the knot.

In the case of a slipknot, one segment of the filament which extends from the knot's free loop, through the body of the knot and to and including the terminus of the filament is referred to as the "standing part." For slipknots then, the more forced bends in the standing part as necessitated by the knot design, the more resistant to slippage and becoming untied the knot in its tightened state tends to be.

In the surgical field, suture knots most certainly should not ordinarily slip nor become untied under any circumstances. It is to knots to be used as sutures in surgical procedures to which Applicant's invention principally relates.

Presently, most suture knots used in surgical procedures are tied completely by hand or, in instanced where the fingers cannot reach, using surgical instruments. Certain apparatuses have been proposed which assist in forming suture knots. However, the prior apparatuses and associated methods of use provide assistance only in tying relatively simple knots or only small portions of more complicated knots.

At present, the most common knots used for sutures are the square and the surgeon's knots. The square knot is a simple knot, but difficult to fashion solely with surgical instruments such as are necessary in endoscopic surgical procedures. Once formed, the square not is not outstanding among knots insofar as resistance to becoming untied is concerned.

Impetus for developing improved knots along with practical methods and apparatuses for their formation arises from the relatively new field of endoscopic surgery. Endoscopic surgery involves making small incisions and passing telescope like instruments to the surgical site. Certain instruments involved permit visualization of internal structures while others effectuate the actual surgical procedure(s).

Current applications of endoscopic surgery include:
  arthroscopic surgery—this form of surgery involves the introduction of instruments into joints, the most common such procedure involving the knee joint, while others involve inspection of many other joints; and
  abdominal surgery—endoscopic abdominal surgery is involved in removing gallbladders and appendices and in performing bowel resections. Gynecologists have been performing endoscopic operations on a regular basis in this country for over twenty years in the form of tubal sterilization procedures. These practitioners also use endoscopic procedures for diagnostic purposes, for freeing up adhesions between various pelvic organs and for correcting conditions leading to infertility. The numerous gynecologic procedures currently performed endoscopically include (1) the use of cautery or laser to destroy abnormal tissue areas, (2) removal of ovarian cysts, (3) removal of certain tumors from the uterus, (4) destruction of pain carrying nerve fibers in patients who have abdominal pain, and (5) procedures requiring knot tying such as bladder suspension operations, hysterectomies and removal of ovaries.

It is anticipated that within the next three to five years 50% of operations that are currently being performed through large abdominal incisions will be performed endoscopically. The advantages of endoscopic surgery are (1) the procedures can be performed on an outpatient, day surgery basis thereby decreasing the cost of prolonged hospitalization and (2) shorter convalescence which allows patients to return to work within a day or two of surgery.

Further advancements and greater utilization of endoscopic procedures is currently hampered by the inability to easily tie knots within the abdominal cavity and other relatively inaccessible involved spaces. Currently, surgery is performed by inserting the needle into a hollow body cavity, passing the needle through the tissues, bringing the needle out to the exterior, manually developing a knot and then locking the knot into position by traction on the end of the apparatus which pulls the thread through a hollow tunnel running the length of a 3 mm nylon tube.

It is anticipated that the inventions disclosed herein will greatly facilitate the tying of extra-corporeal knots (knots being tied outside the body to thereafter be slipped into position). This, in turn, will facilitate and expedite such procedures as: Marshall Marchetti Krantz procedures; uterine suspensions; hysterectomies; appendectomies; and bowel resections. Surgeons required to tie knots at the back of the throat, in the chest cavity, in the placement of heart valves, in brain surgery and in the repair of ligaments (i.e. in arthroscopic surgery) will also be greatly served by the inventions disclosed herein.

It is anticipated that the best mode of practicing all embodiments of Applicant's inventions will involve formation of a protoknot prior to beginning surgery leaving only the passage of one filament element through a specified path for completion of the suture knot. In this manner, the knots will, in all but the rarest of instances, be perfectly formed. This will also allow the surgeon to place sutures more quickly thereby lessening the time that the patient is under anesthesia which has obvious advantages. Absent the complete compliment of Applicant's inventions as disclosed herein, surgeons will be required to use the disclosed knots, if at all, only after the difficult task of tying them completely by hand with the concomitant likelihood of incorrectly forming the knots and thereby increasing the likelihood of slippage.

Prior-issued patents which are known to Applicant and which relate either to surgical knots or to knots in general include the following:

U.S. Pat. No. 2,705,656 issued to Shockey on Apr. 5, 1955 describes a knot tying device for use in mending broken wires as are used in wire sound recorders. The Shockey device constructs a square knot from two loose ends of wire.

U.S. Pat. No. 3,580,256 issued to Wilkinson on May 25, 1971 describes a pre-tied suture and method of suturing that utilizes a pair of butterfly loops in a pre-formed configuration. This pre-tied suture encapsulates the two butterfly loops with a transparent casing and allows the end portions of the suture material to extend from the loops out of the casing. A void remains through the interior of the loops through which one end of the suture material may be passed to finish the formation of the knot. The butterfly loops may then be tightened, the casing forced to disintegrate around it. The knot may then be pulled into a formation that involves a square knot.

U.S. Pat. No. 4,923,461, issued to Caspari on May 8, 1990 discloses a method of suturing for arthroscopic surgery that incorporates a hollow needle and a mechanism whereby suture material may be fed through the hollow needle. Caspari prescribes a series of steps from which a suture knot results.

U.S. Pat. No. 4,602,635, issued to Mulholland on Jul. 29, 1986 discloses a "remote surgical knot tier and method of use" intended for arthroscopic surgery. Mulholland uses a rod-like device through a portion of which extends suture material. Mulholland prescribes a series of steps which ultimately results in the formation of a "square" knot.

U.S. Pat. No. 4,621,640, issued to Mulholland on Nov. 11, 1986, discloses a mechanical needle carrier which is intended to hold and position a surgical needle during arthroscopic surgery. This device is intended to set a stitch at a remote location within the tissue cavity and to then release the needle so that it might be withdrawn from the cavity leaving the suture stitch in place.

U.S. Pat. No. 3,834,395 issued to Santos on Sep. 10, 1974, describes a knot tying instrument which utilizes a pair of elongated rods that face each other and are physically attached to one another in a scissor-like arrangement. The Santos device is designed to tighten a suture knot within in a tissue cavity.

U.S. Pat. No. 2,594,086, issued to Larzelere on Apr. 29, 1952, discloses a surgical instrument designed to tie knots in sutures within body cavities. The Larzelere device is in the nature of an elongated rod with means for engaging two ends of a suture filament so as to direct force appropriately for tightening a square knot.

U.S. Pat. No. 4,711,476, issued to Hansen on Dec. 8, 1987 discloses a knot and various methods for the formation thereof.

Significant limitations relating to previously known apparatuses and methods for the formation of suture knots include: (1) being limited to the formation of simple knots such as the square knot; (2) involving knots which require the manipulation of both ends of a length of suture filament which, accordingly, cannot be substantially tied prior to surgery or merely slipped into place; and (3) requiring multiple manipulations outside of the surgical incision with loops thereby formed being afterwards coaxed toward the suture site.

In addition to the knots and apparatuses disclosed in the above-referenced patents, a knot known as the "Roeder loop" is disclosed by K. Semm in the *Operative Manual for Endoscopic Abdominal Surgery*, Year Book Medical Publishers, Inc., 1987:23–31 which publication will be made available in an information disclosure statement to accompany this application.

SUMMARY OF THE INVENTION

It is an object of the present invention to provide a novel, useful and nonobvious knot for use in surgical procedures.

It is another object of the present invention to provide a novel knot for use in surgical procedures which exhibits more resistance to becoming untied than a square knot when used as the beginning knot of a "running suture".

It is another object of the present invention to provide a novel knot for use in surgical procedures along with simple methods for its formation having significant utility in surgical applications.

It is another object of the present invention to provide a novel and nonobvious method for forming a novel suture knot for use in surgery.

It is another object of the present invention to provide a novel and nonobvious method for forming a novel suture knot which is in the nature of a slipknot which, in turn, can be formed using any elongate member having a channel passing completely through at least a portion thereof.

It is another object of the present invention to provide a suture system which provides a protoknot of a slipknot which can be formed into a finished suture knot by mere passage of the standing part of the protoknot's filament through a tubular member upon which such protoknot is situated.

It is another object of the present invention to provide a suture knot system which is easy to use and which, upon use, results in the formation of a novel and useful suture knot.

In satisfaction of these and related objectives, Applicant's present invention provides a knot which is disclosed herein along with apparatuses and methods for assisting in its formation, all of which were developed by Applicant principally for use in the surgical field.

The knot (the "Weston" knot) is novel and was developed by Applicant. The Weston knot exhibits superior characteristics for use as a suture knot as relate to ease of placement and resistance to slippage once in place. The Weston knot is a slipknot which can be easily formed leaving a large loop and thereafter easily advanced along the filament (so as to close the loop). Once in its finally desired position, pulling on the standing part (the "needle end" as hereafter referenced) while equally and oppositely pushing the knot "locks" the knot thereby preventing further movement or slippage.

Absent direct person-to-person instruction and lengthy practice, the Weston knot is somewhat difficult to tie completely by hand. Accordingly, Applicant also herein provides a very simple method for forming the Weston knot, which method requires only the suture filament and a tubular member in a readily available form.

Still further, Applicant herein discloses suture systems which provide pre-formed protoknots of the Weston knot in configurations which permit rapid completion of sutures during surgical procedures along with knot tighteners (both as part of a suture system and separately) which rapidly and safely tighten and lock a Weston suture knot in place.

All embodiments of Applicant's inventions are drawn toward providing a pre-formed protoknot at a surgical procedure which protoknot becomes the desired suture knot by the simple passage of one end or "standing part" of the suture filament along a specified path through the protoknot. Thereafter the knot is slipped into position and tightened or "locked".

In addition, Applicant's knot is superior in several respects to the above-referenced "Roeder loop": (1) the Roeder loop when complete only exhibits two principle diversions of the standing part of the loop as opposed to the Weston knot's four and is accordingly more likely than the Weston knot to slip; (2) the structure of the Roeder loop is not such as to enable the pre-surgery formation of a protoknot which can thereafter be quickly formed into the finished knot by rapid, straight-line passage of a standing part of the filament through the protoknot; and (3) the Roeder loop is difficult to form during surgery which, in turn, further magnifies limitation (2).

BRIEF DESCRIPTION OF THE DRAWINGS

Applicant's invention may be further understood from a description of the accompanying drawings wherein, unless otherwise specified, like reference numbers are intended to depict like components in the various views.

It is a perspective view of the apex of the knot tightener, and an elevational end view of the apex shown.

Figure 9:
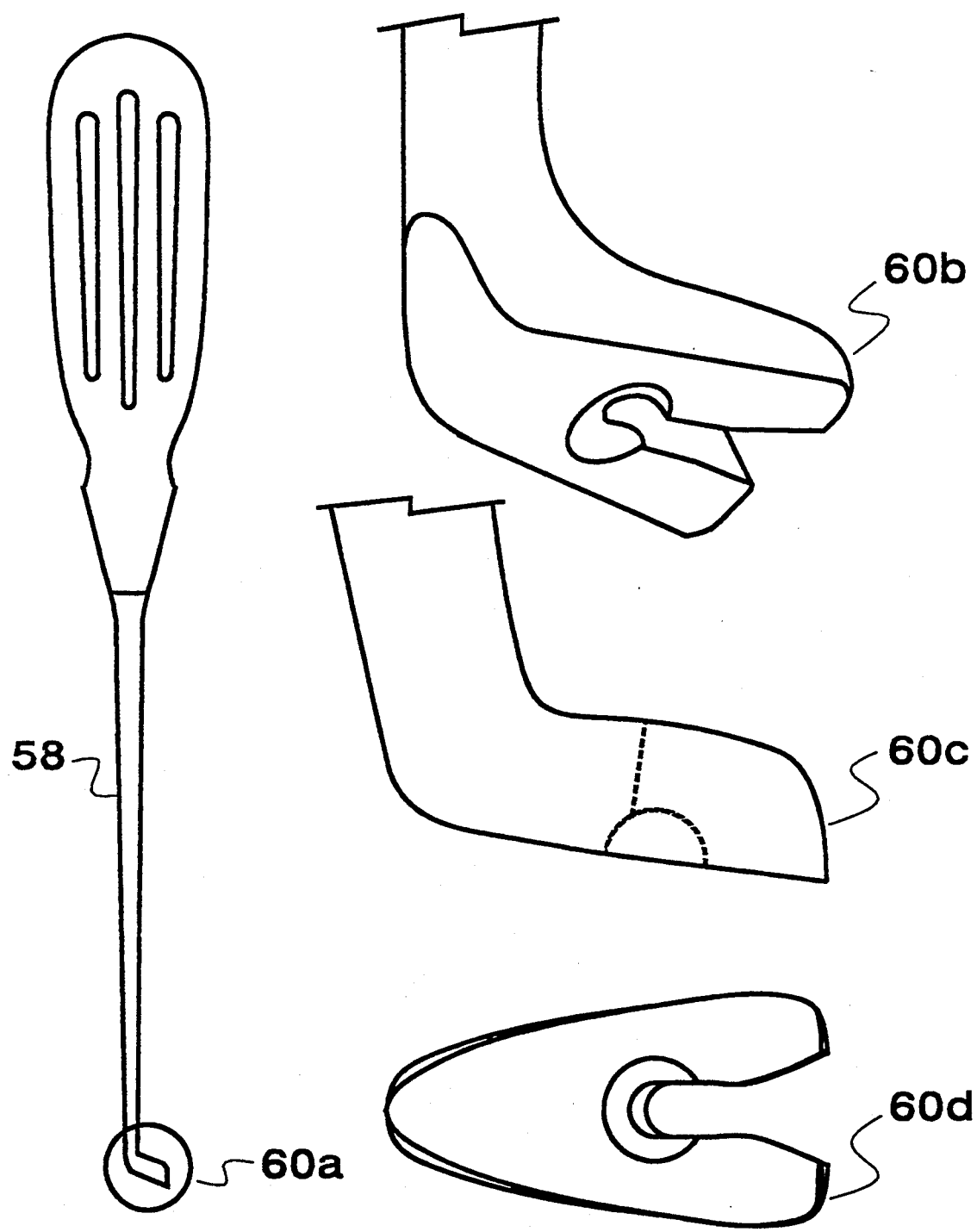
FIG. 9 is an elevational view of an alternative embodiment of a knot tightener for use with slip knots such as the Weston knot herein described.
Figure 10:
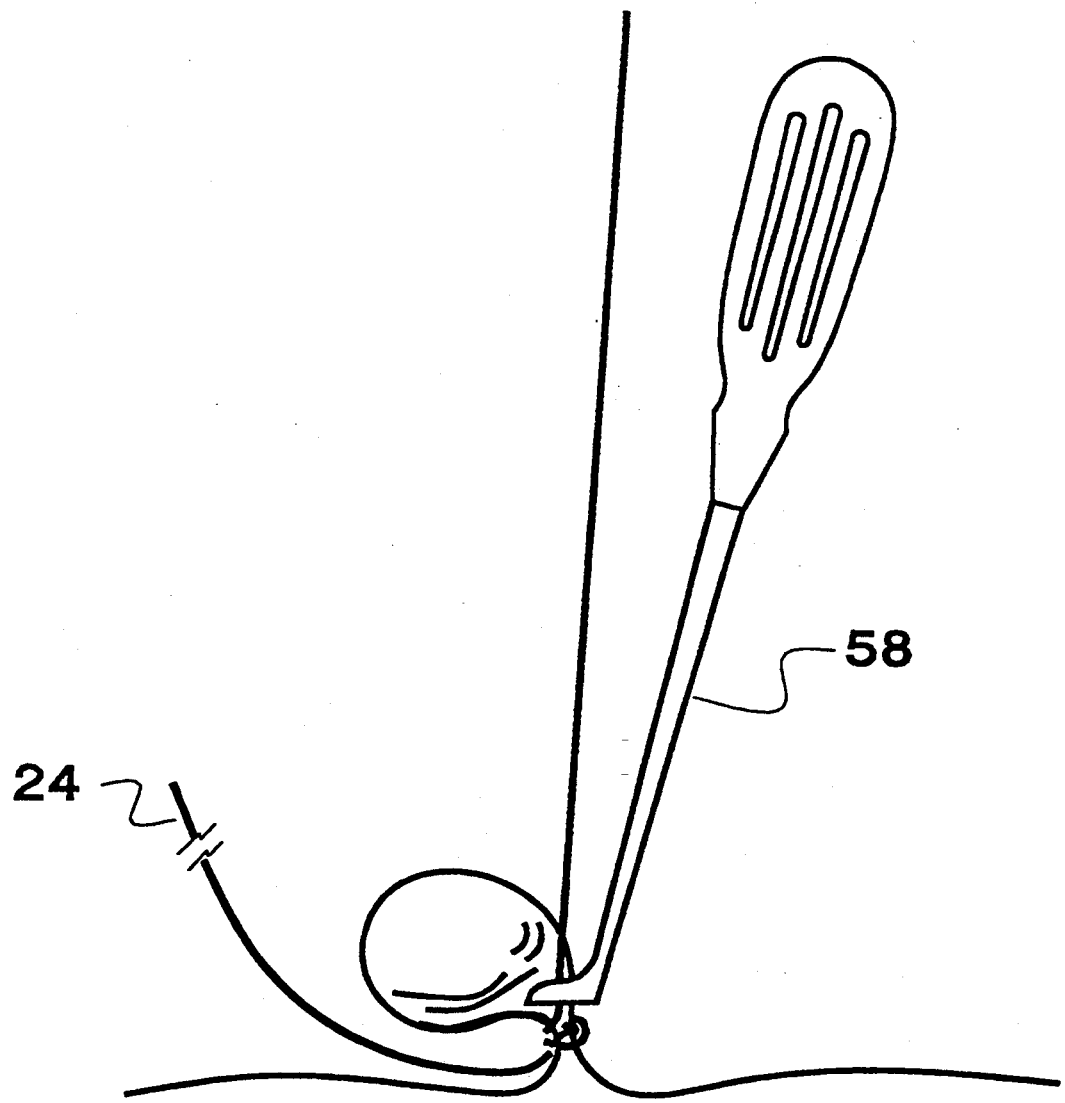

FIG. 10 is a depiction of the knot tightener of FIG. 9a used to encircle and constrict a tissue pedicle during a surgical procedure.

Figure 11:
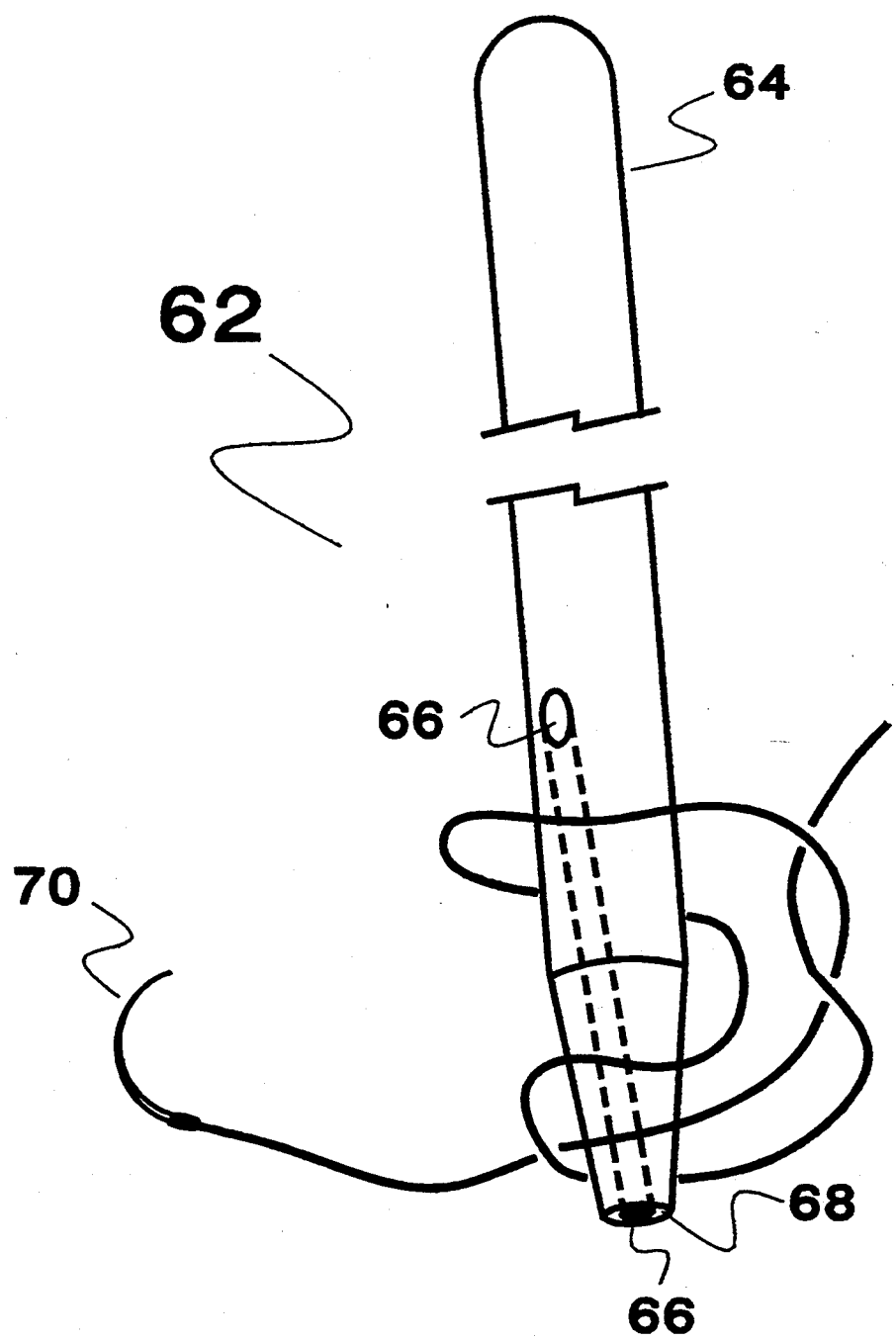

FIG. 11 is a depiction of a pre-formed suture system which incorporates a knot tightener and a pre-formed Weston protoknot (shown in loose formation and without packaging for ease of interpretation).

Figure 12:
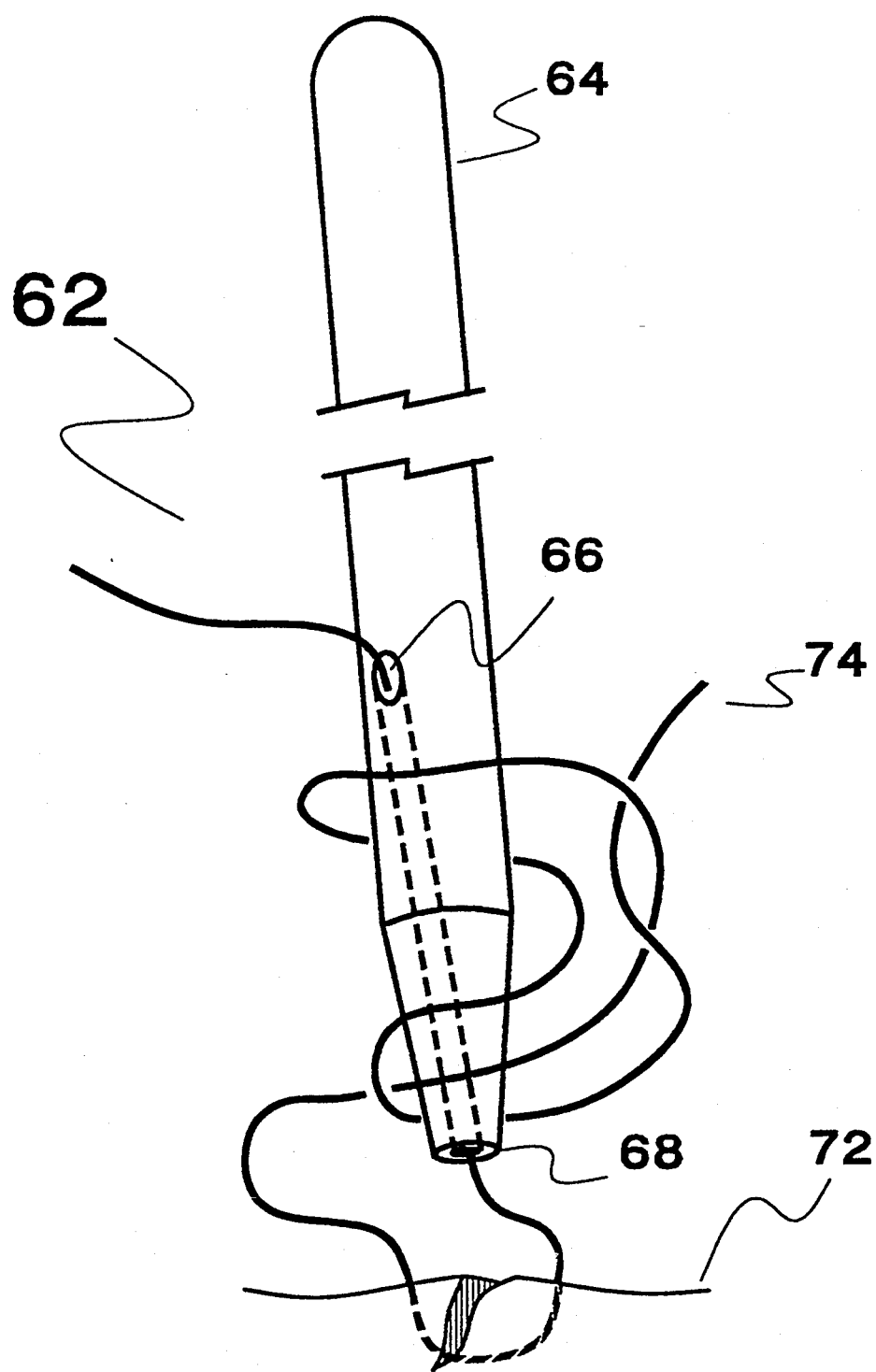

FIG. 12 is a view of FIG. 11 after removal of surgical needle and passage of needle end of filament through channel of tightener.

Figure 13:
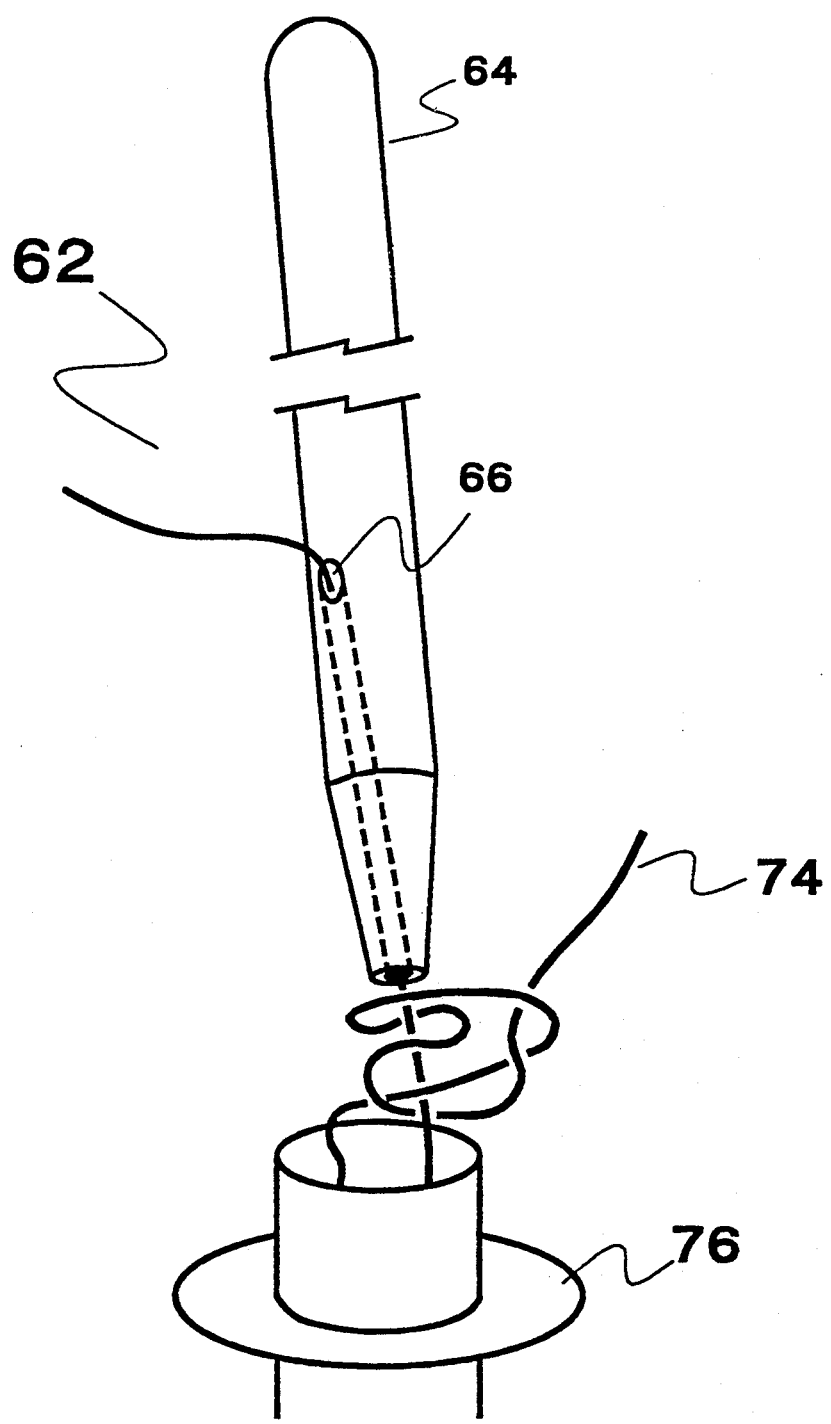

FIG. 13 is a view of a Weston knot slipped from the knot tightener of the pre-formed suture system of FIG. 11 with the suture filament extending into a canula which leads into a bodily cavity to the suture site (not shown).

DETAILED DESCRIPTION OF THE PREFERRED EMBODIMENT

Figure 1:
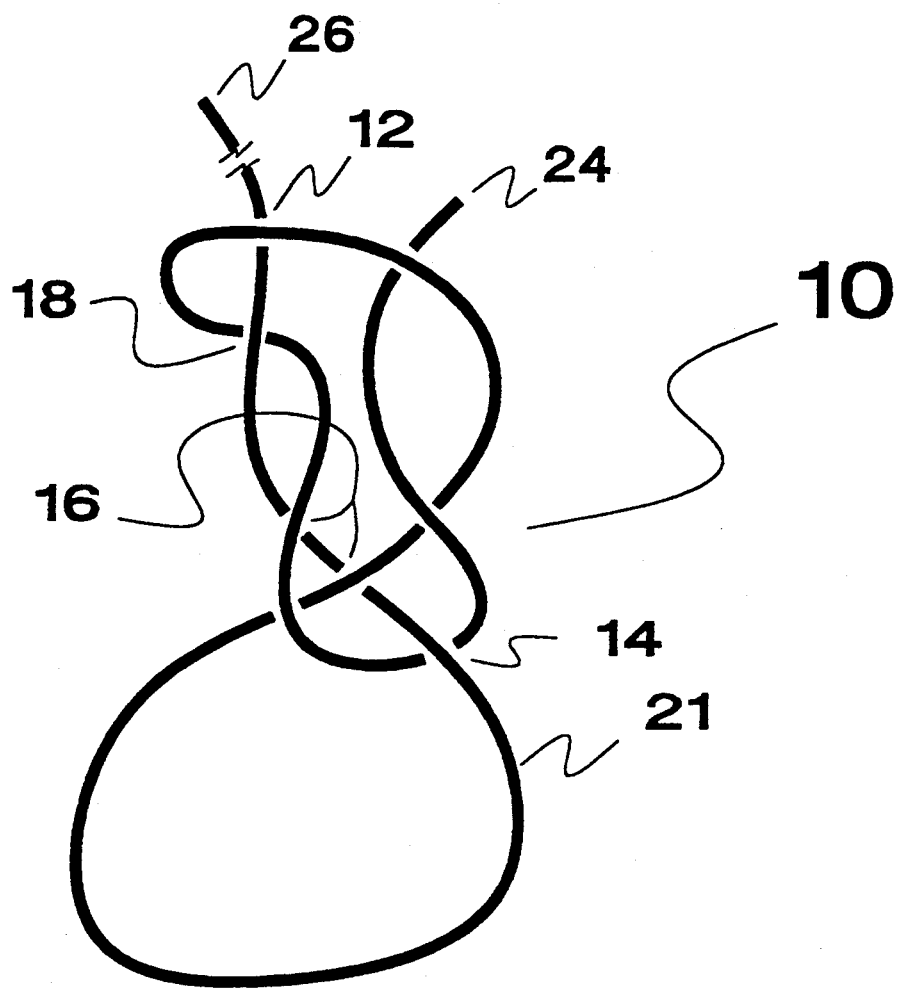
FIG. 1 is an elevational view of a loosely formed Weston knot.

Referring to FIG. 1, the knot of Applicant's invention (the "Weston knot") is depicted (in loose formation) and identified by the reference numeral 10. The stability of the knot when tightened is due to the distortion of the standing part (filament 21) as it is crossed at locations 12, 14, 16, and 18. Accordingly, knot 10 is, in a tightened state, quite stable and unlikely to become loose or unintentionally untied.

To the best of Applicant's knowledge, knot 10 is novel and has utility beyond that of any knot presently used for sutures in the surgical field. No other knot presently used in surgical procedures as a suture knot possesses the characteristics for stability as does the Weston knot. Some examples of suture knots presently in use as well as their method of formation are provided in the above-disclosed United States Patents.

Notwithstanding its great utility as an advancement over knots of the prior art, knot 10 is a complicated knot which is somewhat difficult to tie, or at least to teach others to tie completely by hand. The knot 10 is particularly difficult to tie in the context of surgical procedures in which quite limited space, loss of tactility involved with use of surgical gloves, and time constraints are all factors adverse to utilizing hand-tied, complicated suture knots.

Figure 2:
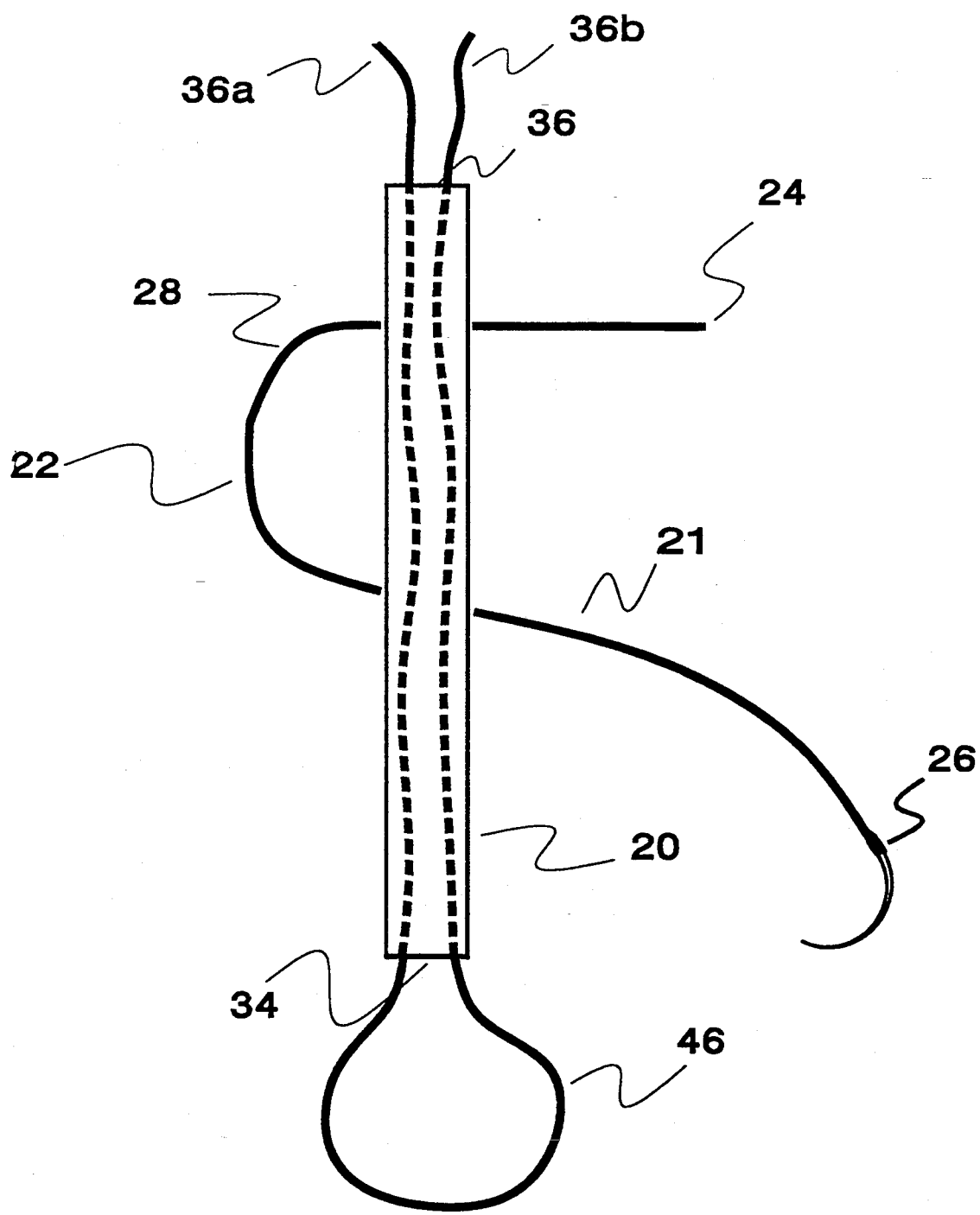
FIG. 2 is an elevational depiction of the relative configuration between a tubular member and a filament at an early stage of forming a Weston knot.

Accordingly, Applicant herein prescribes a method, easily taught and learned, by which knot 10 can be formed with a minimum of effort. Referring initially to FIG. 2, the use of a tube member 20 greatly facilitates the formation of knot 10 from a filament 21. A simple soda straw is perhaps the preferable tubular member to be used in teaching the formation of knot 10 or when practicing the same, however, any elongate member having openings separated along its elongate axis may be equally acceptable (as in the case of the knot tightener to be described hereafter).

Figure 3:
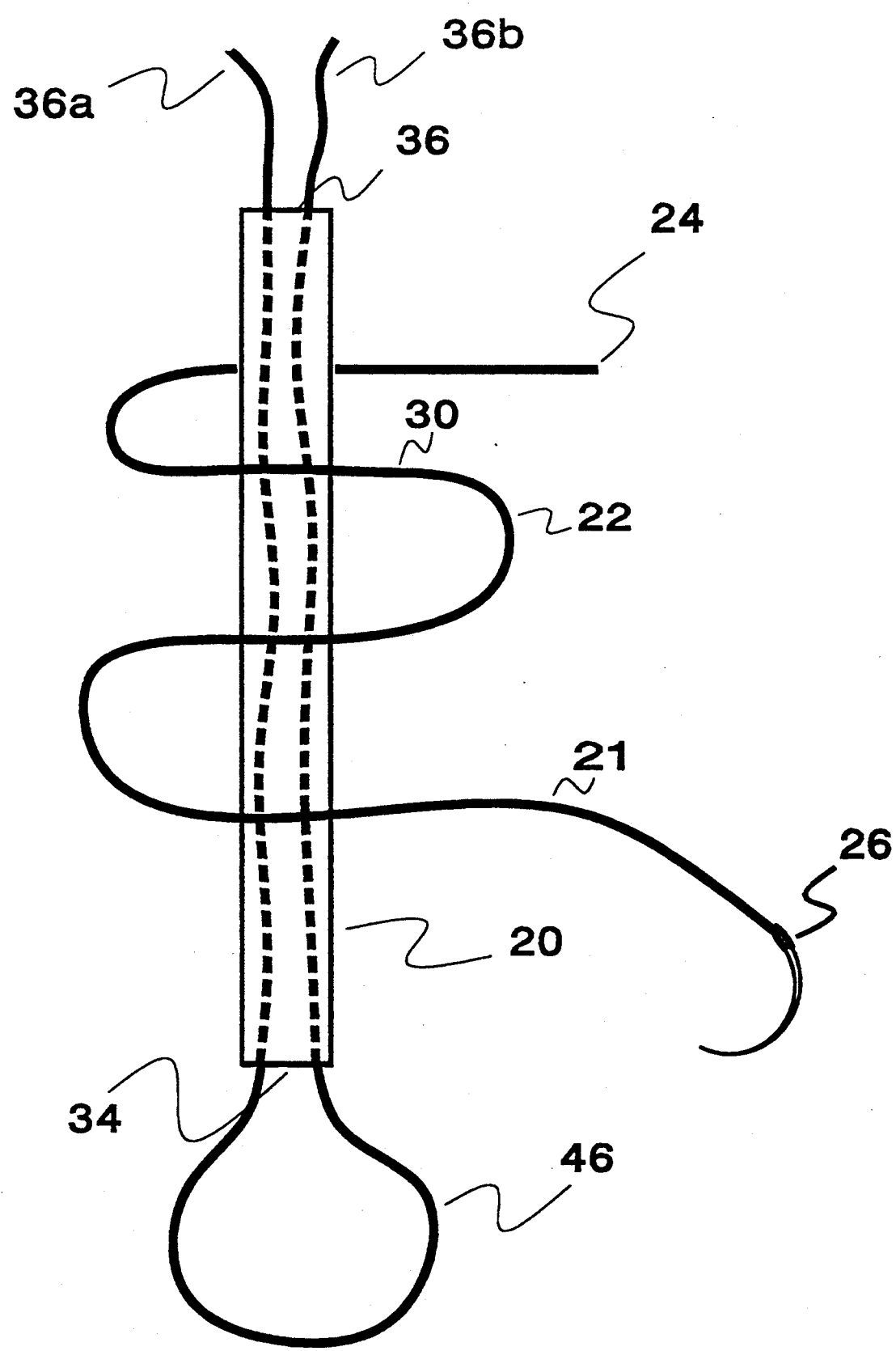
FIG. 3 is an elevation depiction of the relative configuration between a tubular member and a filament at an intermediate stage of forming a Weston knot.
Figure 4:
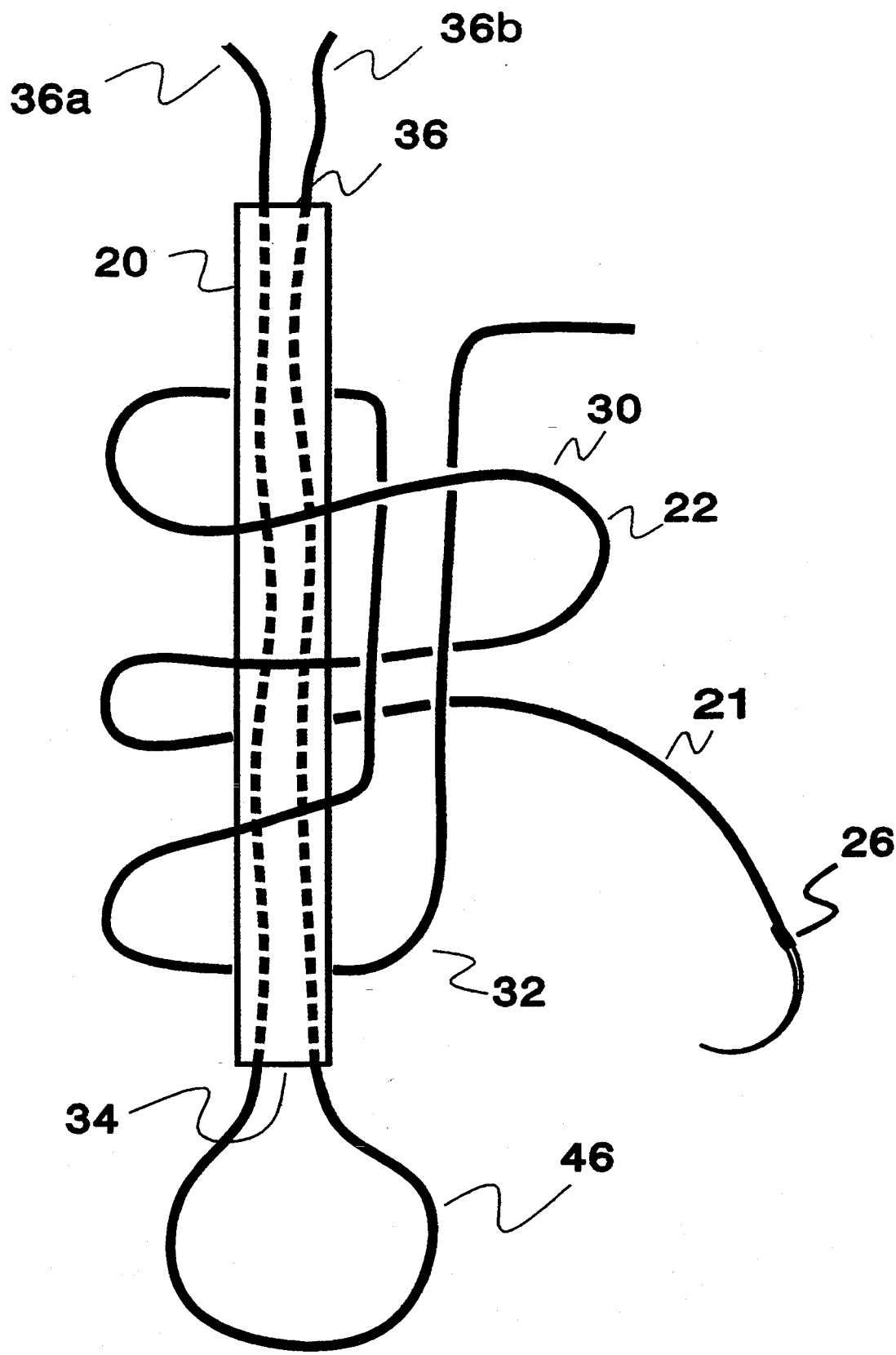
FIG. 4 is an elevation depiction of the relative configuration between a tubular member and a filament at an near concluding stage of forming a Weston knot.

The following description of a method for forming knot 10 from a filament 21 using tube member 20 will be made as if from the user's perspective looking straight forward at the filament 21 and the tube member 20 in the user's hands. Reference to FIGS. 2, 3, and 4 will assist the reader in ascertaining the manipulation to the filament 21 which occurs during the prescribed steps. Passing through the tube member 20 is a double D strand of nylon fishing line forming a loop 46 at end 34 of tubular member 20 with two strands 36a and 36b extending from the other end 36 of tubular member 20.

With the tube member 20 in an upright orientation, double a length of filament 21 behind the tube member 20 such that a first filament bight 22 is formed behind and to the user's left of the tube member 20, and the two lengths of filament 21 either side of the bight (the shorter terminal segment 24 and the longer needle segment 26) extend (at least in part) horizontally behind and to the user's right of the tube member 20 with the terminal segment 24 of the filament 21 in the superior position and spaced approximately one inch from the needle segment 26 of the filament 21 which is in the inferior position.

Stabilizing this filament 21 configuration against the rearward side of the tube member 20 with the right hand, the user should next bring his left index finger and left thumb through the space 28 defined by the first filament bight 22 and the left edge of the tube member 20, beginning distant most from the user and progressing toward the user and with the index finger in the superior position.

Next, the user's left index finger and left thumb should move from left to right around the tube member 20 until a length of the terminal segment 24 of the filament 21 may be grasped to the right side of the tube member 20 (at this point, the user should be grasping the terminal segment 24 of the filament 21 with the left index finger and left thumb extending away from the user). A portion of the terminal segment 24 should be drawn through the space 30 defined by the first filament bight 22 and the right edge of the tube member 20 thereby forming a second filament bight 32.

The user should next, while maintaining the grasping finger and thumb oriented away from his body so as not to twist the second filament bight 32, pass the second filament bight 32, moving away from the user, over the lowermost end of the tube member 20. This completes formations of the protoknot of the Weston Knot. For the right handed user, the user should next immobilize the filament 21 configuration relative to the tube with the left hand. To then complete the Weston knot 10, the needle segment 26 of the filament 21 is passed through the tube member 20 from the lower tube end 34 to the upper tube end 36 completing formation of the knot 10. The tube member 20 is then removed (by sliding it over the needle end 26 of the filament 21 with the knot 10 only to be suitably tightened thereafter.

Figure 6:
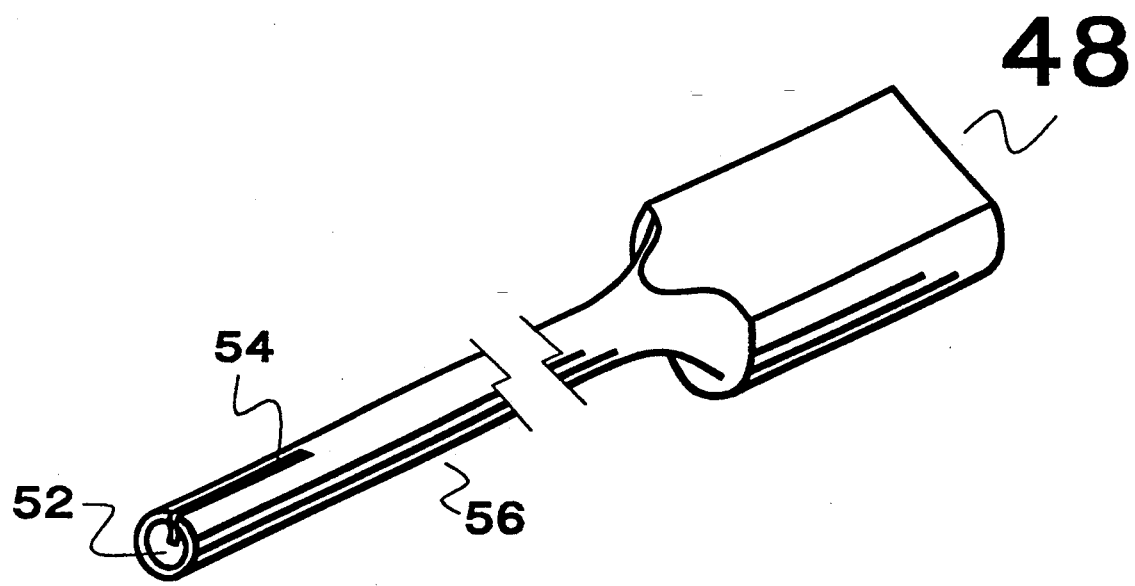
FIG. 6 is an elevational view of a knot tightener as disclosed herein.
Figure 7:
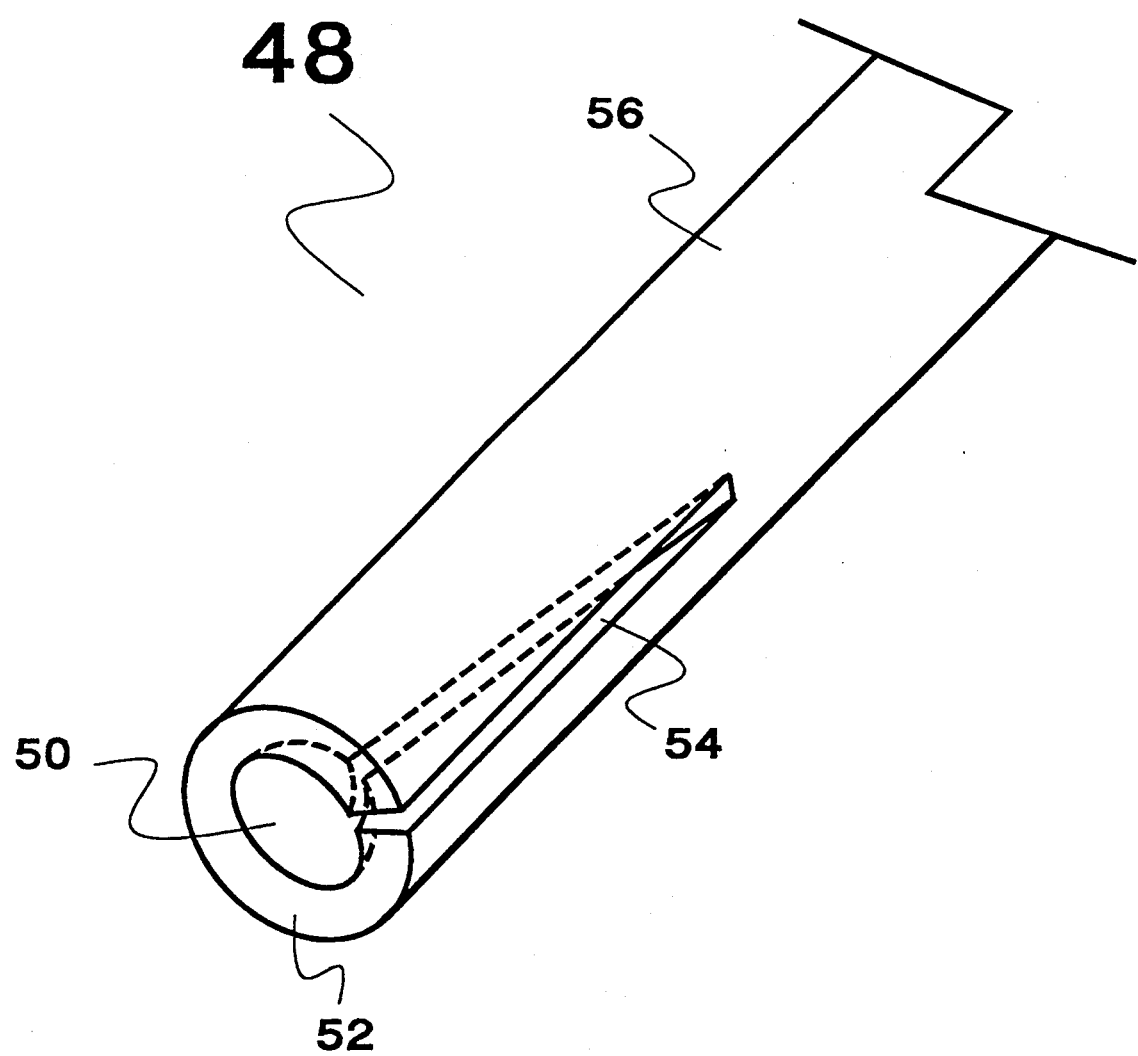
FIG. 7 is a perspective view of the apex of the knot tightener of FIG. 6.
Figure 8:
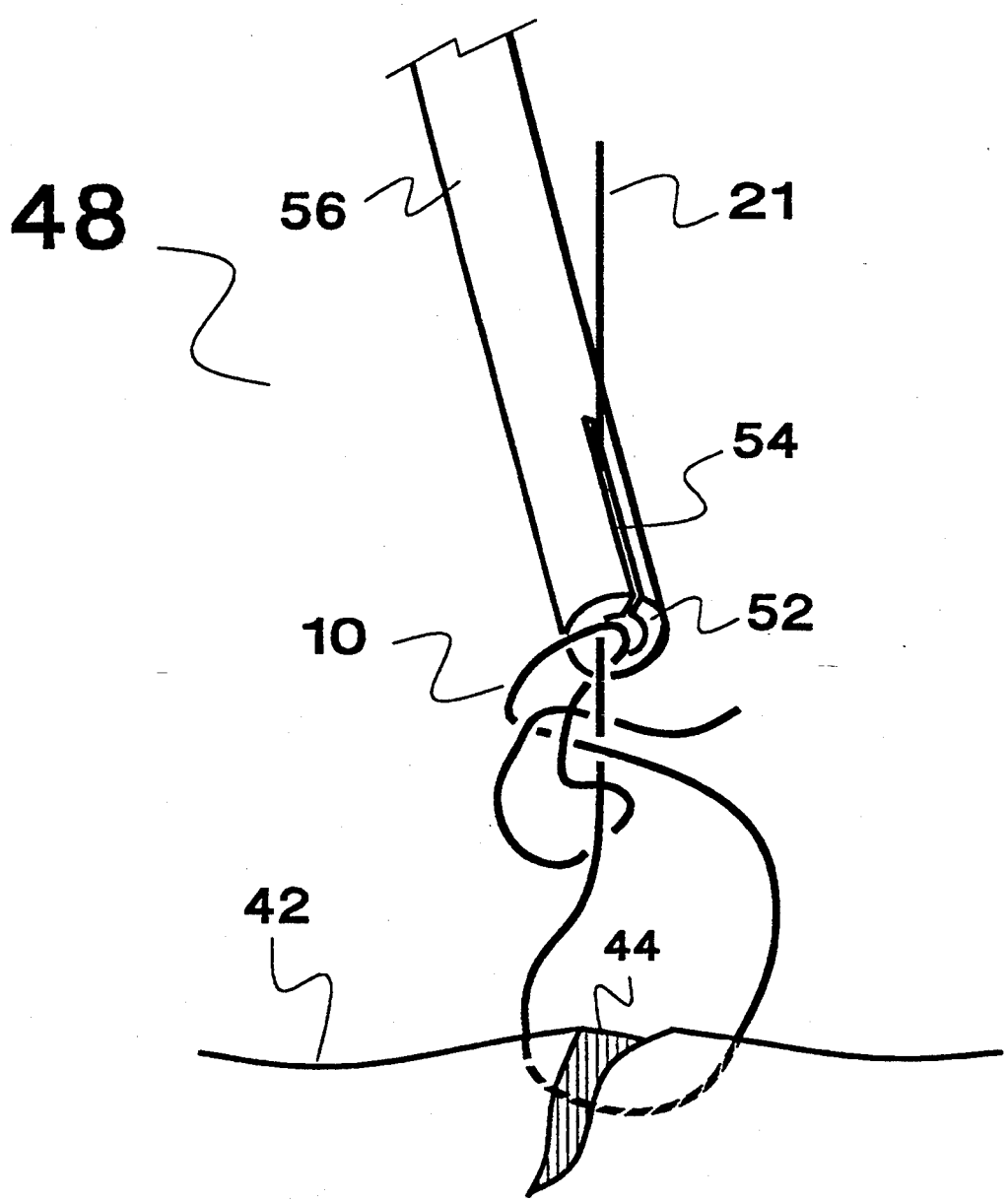
FIG. 8 is a perspective view of the apex of a knot tightener of FIG. 6 depicted as being used to push a suture knot into place for tightening such knot.

Referring to FIGS. 6, 7, and 8, the latter-mentioned step, tightening knot 10 against the tissue 42, may be achieved using a knot tightener 48. As depicted, knot tightener 48 exhibits an indentation 50 at its apex 52. An elongate recess 54 is oriented oblique relative to the long axis of the tightener 48. The recess 54 terminates at one of its two ends at the indentation 50 and at the other of its two ends as an opening in the shaft 56 of the tightener 48. This permits the tightener 48 to be pushed against the knot 10 sufficient to set the knot 10 against the tissue 42. The tightener 48 can then be removed by simply allowing the filament 21 to exit the tightener 48 through the open recess 54.

Referring to FIGS. 9 and 10, a different embodiment of a knot tightener 58 is shown for use in certain surgical procedures involving the snaring of a tissue protrusion, such as a polyp. The operation of tightener 58 is substantially similar to that of tightener 48, but due to the differing configuration of apex 60, it assists in tightening an already formed Weston knot 10 over a tissue protrusion. Still another embodiment of a tightener useful in such situations is depicted in FIG. 11 and identified by the reference numeral 64.

It is expected that certain practitioners will prefer to form the Weston knot by the above-described tubular member-based methods. However, others who fully appreciate the utility and benefits of this knot in the surgical context may prefer that it be made available in the most easily used form possible.

In addressing the latter practitioners, Applicant suggests suture knot systems which include pre-formed suture protoknot units along with knot tighteners as are appropriate to the particular surgical procedure for which the system is intended.

Figure 5:
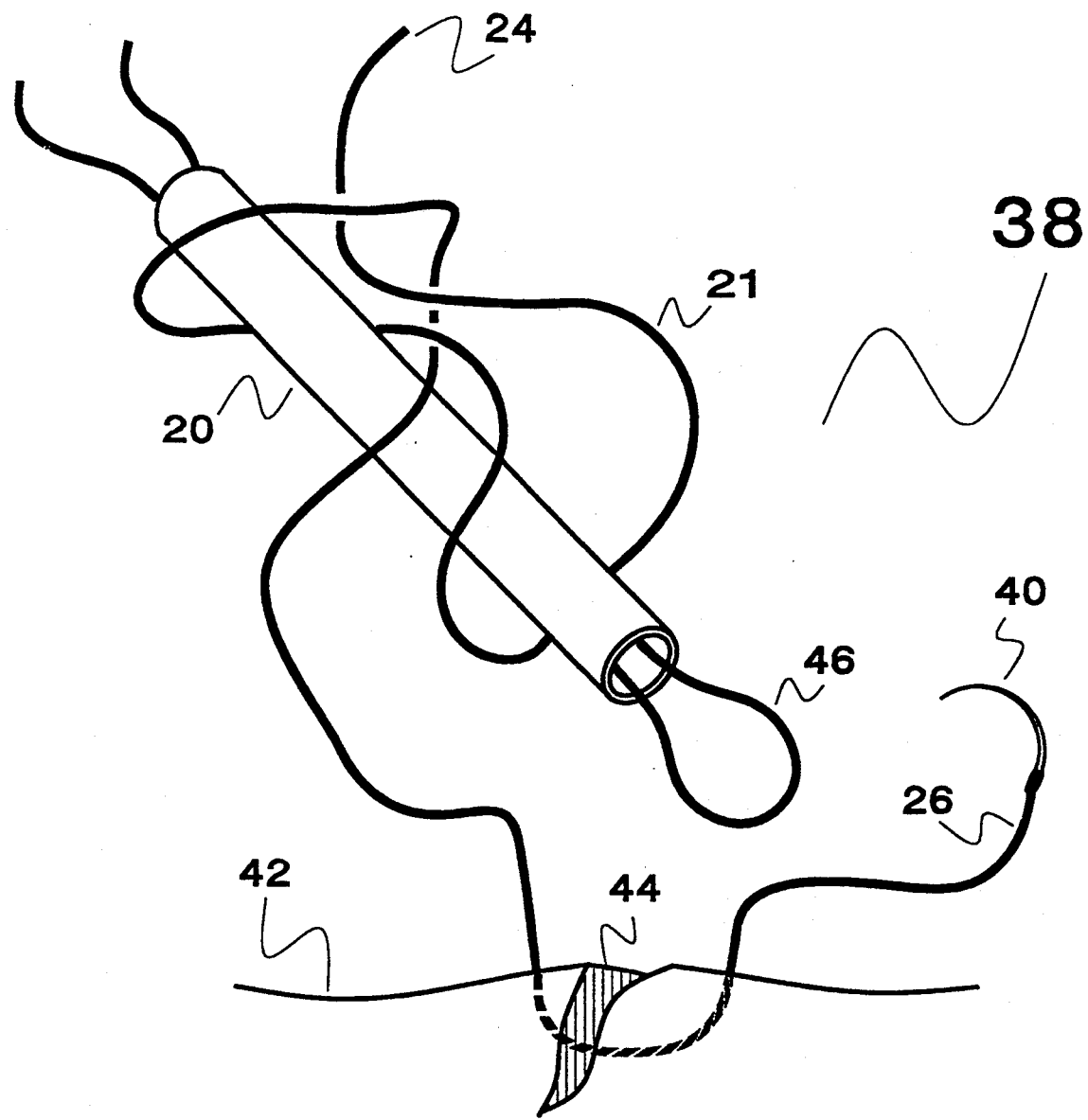
FIG. 5 is a depiction of a suture protoknot unit for formation of a Weston knot during a surgical procedure.

Referring to FIG. 5, a pre-packaged Weston knot suture unit 38 is suggested. With the filament 21 suitably immobilized relative to the tube member 20 through temporary affixation to a rigid platform (not shown in the drawing) such as sterilized fiberboard, a pre-formed protoknot for the Weston knot 10 may be marketed to the medical field. The filament 21 of such a unit 38 would have a suture needle 40 affixed to the needle end 26 of the filament 21. The filament 21 would ideally be made available in a variety of suture materials and sizes.

As depicted in FIG. 5, use of such a unit 38 would merely involve removing it from its packaging, passing the needle 40 through the patient's tissue 42 in appropriate relation to the incision 44 to be closed, and then, using a threading loop 46 (supplied with the unit), drawing the needle end 26 of the filament 21 through the tube member 20 to complete the knot 10 as a suture. Thereafter only tightening the suture adjacent to the tissue 42 would remain.

Referring to FIGS. 11–13, an alternative pre-formed suture system 62 would incorporate a knot tightener 64 which itself would serve as the tubular member such as tubular member 20 of FIG. 5. The knot tightener 64 exhibits a channel 66 which passes through the tightener extending from the tightener tip 68 to a point on the shaft of the tightener 64 and being open at both ends. One making the pre-formed suture system 62 would use the tightener 64 in a manner analogous to that of using the tubular member 21 in tying the Weston knot as described above, Once the Weston protoknot is formed on the tightener 64, the protoknot should positioned on the shaft of the tightener 64 between its tip 68 and the opening to the channel 66 on the shaft of the tightener 64. In this manner, once the surgical needle 70 is passed through the patient's tissue 72, the needle 70 is cut and removed from the filament 74 and the needle end 76 of the filament 74 is passed through the channel 66 moving from the channel opening at the tip 68 to the opening on the shaft of the tightener 64. This corresponds to passing the needle end segment 26 of the filament 21 through the tubular member 20 as described above with reference to FIGS. 5 and 6.

To be practical for pre-packaging, the properly positioned Weston protoknot should be reversibly immobilized relative to the tightener 64 so that the protoknot does not slip from the tightener 64 prematurely. An easily removed, shrink-wrapped, medically acceptable plastic sheath about the protoknot (not shown in the drawings) would constitute one avenue for immobilization.

The pre-formed suture system 62 depicted in FIGS. 11–13 has extraordinary utility in surgical procedures involving limited access to the suture site. In order to use the Weston knot with its clear benefits, the surgeon need merely remove the system 62 from its outer packaging (not depicted in the drawings), pass the needle 70 through the affected tissue 72, thread the filament 74 (with the needle 70 removed) through the channel 66 of the tightener 64, slide the tightener 64 from the filament 74 (as shown in FIG. 13), and set the knot with the tightener 64.

Referring specifically to FIG. 13, a canula 78 is shown in proximity to the pre-formed suture system 62 as in the case of endoscopic surgery where the suture knot is to be set well within a body cavity through an incision which makes direct access impossible. It is in precisely such a situation where the pre-formed suture system 62 with the incorporated knot tightener 64 provides the greatest convenience, reliability and time savings. The knot, being in the nature of a slipknot, can simply be guided through the canula 78 by the knot tightener 64, and when in position "locked" by pulling the needle end 76 of the filament 74 and pushing against the knot with the tightener 64 with equal and opposing force.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method for forming a knot comprising the steps of:

selecting a tubular member and a filament, said tubular member having a first and a second tube end;

with the long axis of said tubular member situated in a substantially fixed reference orientation in a first plane (such as a vertical orientation relative to an individual forming said knot), doubling a length of said filament adjacent to said tubular member and on a first side of said tubular member (such as a side of said tubular member opposite from said individual) such that a first filament bight is formed at a first bight point situated on said first side of said tubular member and separated from said tubular member in substantially a first lateral direction from said tubular member, said first lateral direction being orthogonal to said fixed reference orientation (such as to the left of said tubular member from said individual's perspective) with a first terminal length of said filament and a second needle length of said filament extending from said either side of said first filament bight beyond and perpendicular to said tubular member in a second lateral direction orthogonal to said fixed reference orientation and substantially opposite said first lateral direction (such as behind said tubular member and toward the right thereof from said individual's perspective), said needle length and said terminal length lying substantially in a single second plane parallel with said first plane of said fixed reference orientation, said terminal segment lying closer to said first tube end than said needle segment and being separated from said needle segment by approximately one inch;

moving said first filament bight substantially in said second lateral direction and across a second side of said tubular member, said second side being opposite said first side, so as to partially encircle said tubular member and ending such movement whereby said first bight comes to overlie a portion of said needle segment and of said terminal segment of said filament at points in said second lateral direction from said tubular member;

grasping a loop segment of said terminal segment, said loop segment being situated at a loop segment point substantially on said first side of and in said second lateral direction from said tubular member, and drawing said loop segment through a space the perimeter of which space is jointly defined by said first filament bight and said tubular member and lying in said second direction from said tubular member and moving said loop segment through said space from said first side to said second side of said tubular member thereby forming a second filament bight from said loop segment of said terminal segment;

passing said second filament bight over said second tube end moving from said second side to said first side of said tubular member; and passing said needle segment of said filament through said tubular member moving from said second tube end to said first tube end.

2. A method of suturing tissue comprising the steps of:

selecting a channel member having an elongate channel passing therethrough, said channel exiting said channel member at first and second channel openings;

insuring that said channel member has a slipknot protoknot situated thereon, said slipknot protoknot being formed from a filament having a terminal filament end and a needle filament end, said slipknot protoknot to be situated between said first and second channel openings on said channel member and configured relative to said channel member whereby passing said needle filament end through said channel entering at said first channel opening and exiting said second channel opening and thereafter removing said channel member from said filament at said needle filament end forms a slipknot, said slipknot protoknot being a protoknot for a Weston knot which may be formed as follows:

selecting a tubular member and a filament, said tubular member having a first and a second tube end;

with the long axis of said tubular member situated in a fixed reference orientation in a first plane (such as a vertical orientation relative to an individual forming said knot), doubling a length of said filament adjacent to said tubular member and on a first side of said tubular member (such as a side of said tubular member opposite from said individual) such that a first filament bight is formed at a first bight point situated on said first side of said tubular member and separated from said tubular member in substantially a first lateral direction from said tubular member, said first lateral direction being orthogonal to said fixed reference orientation (such as to the left of said tubular member from said individual's perspective) with a first terminal length of said filament and a second needle length of said filament extending from said first filament bight beyond and perpendicular to said tubular member in a second lateral direction orthogonal to said fixed reference orientation and substantially opposite said first lateral direction (such as behind said tubular member and toward the right thereof from said individual's perspective), said needle length and said terminal length lying substantially in a single second plane parallel with said first plane of said fixed reference orientation, said terminal segment lying closer to said first tube end than said needle segment and being separated from said needle segment by approximately one inch;

moving said first filament bight substantially in said second lateral direction and across a second side of said tubular member, said second side being opposite said first side, so as to partially encircle said tubular member and ending such movement whereby said first bight comes to overlie a portion of said needle segment and of said terminal segment of said filament at points in said second lateral direction from said tubular member;

grasping a loop segment of said terminal segment, said loop segment being situated at a loop segment point substantially on said first side of and in said second lateral direction from said tubular member, and drawing said loop segment through a space the perimeter of which space is jointly defined by said first filament bight and said tubular member and lying in said second direction from said tubular member and moving said loop segment through said space from said first side to said second side of said tubular member thereby forming a second filament bight from said loop segment of said terminal segment;

passing said second filament bight over said second tube end moving from said second side to said first side of said tubular member; and passing said needle segment of said filament through said tubular member moving from said second tube end to said first tube end;

passing said needle filament end of said filament through tissue to be sutured;

passing said needle filament end of said filament through said channel of said channel member entering at said first channel opening and exiting at said second channel opening;

separating said channel member from said filament by removing said channel member from said filament at said needle filament end; and tightening said slipknot against said tissue.

3. A knot which may be formed from the following steps:

selecting a tubular member and a filament, said tubular member having a first and a second tube end;

with the long axis of said tubular member situated in a fixed reference orientation in a first plane (such as a vertical orientation relative to an individual forming said knot), doubling a length of said filament adjacent to said tubular member and on a first side of said tubular member (such as a side of said tubular member opposite from said individual) such that a first filament bight is formed at a first bight point situated on said first side of said tubular member and separated from said tubular member in substantially a first lateral direction from said tubular member, said first lateral direction being orthogonal to said fixed reference orientation (such as to the left of said tubular member from said individual's perspective) with a first terminal length of said filament and a second needle length of said filament extending from said first filament bight beyond and perpendicular to said tubular member in a second lateral direction orthogonal to said fixed reference orientation and substantially opposite said first lateral direction (such as behind said tubular member and toward the right thereof from said individual's perspective), said needle length and said terminal length lying substantially in a single plane parallel with said first plane of said fixed reference orientation, said terminal segment lying closer to said first tube end than said needle segment and being separated from said needle segment by approximately one inch;

moving said first filament bight substantially in said second lateral direction and across a second side of said tubular member, said second side being opposite said first side, so as to partially encircle said tubular member and ending such movement whereby said first bight comes to overlie a portion of said needle segment and of said terminal segment of said filament at points in said second lateral direction from said tubular member;

grasping a loop segment of said terminal segment, said loop segment being situated at a loop segment point substantially on said first side of and in said second lateral direction from said tubular member, and drawing said loop segment through a space the perimeter of which space is jointly defined by said first filament bight and said tubular member and lying in said second direction from said tubular member and moving said loop segment through said space from said first side to said second side of said tubular member thereby forming a second filament bight from said loop segment of said terminal segment;

passing said second filament bight over said second tube end moving from said second side to said first side of said tubular member; and passing said needle segment of said filament through said tubular member moving from said second tube end to said first tube end.

4. A pre-formed suture system comprising:

an elongate channel member having a channel passing therethrough, said channel being open at first and second channel ends of said channel;

a protoknot, said protoknot being formed from a filament and being positioned on said channel member whereby passing a first end of said filament through said channel by entering at said first channel end and exiting at said second channel end and removing said channel member from said filament completes formation of a slipknot, said slipknot being a Weston knot which may be formed by the following steps:

selecting a tubular member and a filament, said tubular member having a first and a second tube end;

with the long axis of said tubular member situated in a fixed reference orientation in a first plane (such as a vertical orientation relative to an individual forming said knot), doubling a length of said filament adjacent to said tubular member and on a first side of said tubular member (such as a side of said tubular member opposite from said individual) such that a first filament bight is formed at a first bight point situated on said first side of said tubular member and separated from said tubular member in substantially a first lateral direction from said tubular member, said first lateral direction being orthogonal to said fixed reference orientation (such as to the left of said tubular member from said individual's perspective) with a first terminal length of said filament and a second needle length of said filament extending from said first filament bight beyond and perpendicular to said tubular member in a second lateral direction orthogonal to said fixed reference orientation and substantially opposite said first lateral direction (such as behind said tubular member and toward the right thereof from said individual's perspective), said needle length and said terminal length lying substantially in a single second plane parallel with said first plane of said fixed reference orientation, said terminal segment lying closer to said first tube end than said needle segment and being separated from said needle segment by approximately one inch;

moving said first filament bight substantially in said second lateral direction and across a second side of said tubular member, said second side being opposite said first side, so as to partially encircle said tubular member and ending such movement whereby said first bight comes to overlie a portion of said needle segment and of said terminal segment of said filament at points in said second lateral direction from said tubular member;

grasping a loop segment of said terminal segment, said loop segment being situated at a loop segment point substantially on said first side of and in said second lateral direction from said tubular member, and drawing said loop segment through a space the perimeter of which space is jointly defined by said first filament bight and said tubular member and lying in said second direction from said tubular member and moving said loop segment through said space from said first side to said second side of said tubular member thereby forming a second filament bight from said loop segment of said terminal segment;

passing said second filament bight over said second tube end moving from said second side to said first side of said tubular member; and passing said needle segment of said filament through said tubular member moving from said second tube end to said first tube end;

said elongate channel member being a knot tightener, said knot tightener being substantially rigid, and having a handle portion and means for at least partially enveloping said slipknot for facilitating the advancement of said slipknot, once formed, along said filament toward said suture site for facilitating the tightening of said slipknot at said suture site.

* * * * *